Figure 1:
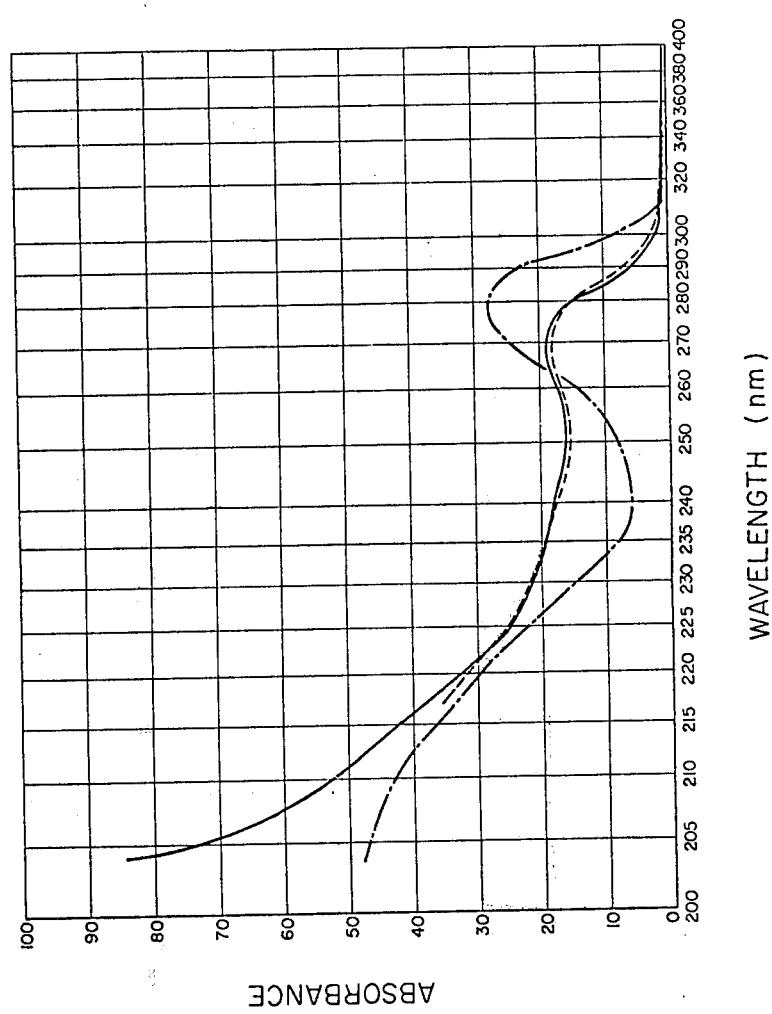

United States Patent [19]

Kishi et al.

[11] 4,007,267
[45] Feb. 8, 1977

[54] ANTIBIOTIC B-98891

[75] Inventors: Toyokazu Kishi, Nara; Takashi Iwasa, Kyoto; Taiki Kusaka; Setsuo Harada, both of Hyogo, all of Japan

[73] Assignee: Takeda Chemical Industries, Ltd., Osaka, Japan

[22] Filed: Mar. 28, 1975

[21] Appl. No.: 562,935

[30] Foreign Application Priority Data

Mar. 28, 1974 Japan .............................. 49-35254

[52] U.S. Cl. .............................. 424/116; 195/80 R
[51] Int. Cl.² ......................................... H61K 35/74
[58] Field of Search ................... 424/116; 195/80 R

[56] References Cited

UNITED STATES PATENTS 3,691,279  9/1972  Thompson et al. ................ 424/116

*Primary Examiner*—Jerome D. Goldberg
*Attorney, Agent, or Firm*—Wenderoth, Lind & Ponack

[57] ABSTRACT

A novel antibiotic B-98891, which is produced by culturing a strain of microorganisms belonging to the genus Streptomyces, shows remarkable combatting effect against microorganisms causing plant diseases. Compositions containing the antibiotic are useful for controlling diseases in plants with less undesirable side effects.

9 Claims, 2 Drawing Figures

ANTIBIOTIC B-98891

The present invention relates to a new antibiotic. More particularly, the invention provides a new antibiotic B-98891 which is obtained by cultivating the antibiotic B-98891-producing strain belonging to the genus Streptomyces, and salts thereof.

In search of new antibiotic substances, the present inventors isolated a large number of soil microorganisms and studied their biologically active metabolites. The research work led to the finding that certain soil microorganisms are capable of producing a new antibiotic designated as B-98891, that these microorganisms belong to the genus Streptomyces and that it is possible to obtain said antibiotic by cultivating these microorganisms so that the said antibiotic may be accumulated in the culture medium.

Thus, the invention relates to a new antibiotic, which is produced by cultivating a B-98891-producing strain belonging to the genus Streptomyces so that the said antibiotic is produced and accumulated in the fermented broth, and recovering the antibiotic so accumulated from said fermented broth.

Furthermore, it is found unexpectedly that the new antibiotic B-98891 shows an excellent controlling effect against plant diseases, for example, powdery mildew.

It is the principal object of this invention to provide new antibiotic B-98891 and the method of preparing the same.

Another object is to provide a fungicide for combatting plant diseases showing no substantial phytotoxicity which is substantially non-toxic against animals as well as fish.

Further object is to provide a concentrate of said fungicide, which is applicable, simply diluted at the use, to plants for the same purpose as mentioned just above, and which is more stable and more convenient in storage or transport than the diluted composition for the ready use.

Other objects will be apparent from the description detailed hereinafter in this specification.

The antibiotic B-98891 is obtained by cultivation of B-98891-producing strain belonging to the genus Streptomyces so long as it is capable of producing the antibiotic B-98891. For example, the strain which was isolated from the soil collected in New Guinea by the present inventors, classified as a strain of *Streptomyces rimofaciens*, and named *Streptomyces rimofaciens* No. B-98891, as well as its related strain, may be employed to particular advantage.

Some of the microbiological and cultural characteristics of *Streptomyces rimofaciens* No. B-98891 are shown below.

1. Morphological characteristics

On various culture media, this strain forms an aerial mycelium and branching type of the spore-bearing hyphae is Biverticillus. Though rarely, loops and hooks are also found (not on the verticils) on glucose asparagine agar. The shape of the spore is ovoid to cylindrical, its size ranging from $0.6 - 0.8 \times 0.7 - 1.3 \mu$. The spores normally occur in chains of 3 to 16, the surface of each spore being smooth or warty. On various culture media, none of sporangium, flagella, sclerotium, etc. are observed.

2. Cultural characteristics

The cultural characteristics of the present strain are shown in Table 1. Unless otherwise indicated, the descriptions are the results of cultivation at 28° C for 21 days. Color names in the tables are based on Color Harmony Manual, 4th ed., Container Corporation of America.

Table 1

Cultural characteristics of Streptomyces rimofaciens No.B-98891 on various media

| Medium | *Characteristics |
|---|---|
| Sucrose nitrate agar | G : Colorless, penetrating into medium |
| | R : White to Light Ivory (2 ca) |
| | AM : Scant, cottony, Shell (3 ca) |
| | SP : None |
| Glucose nitrate agar | G : Colorless, penetrating into medium |
| | R : Yellow Maple (3 ng) |
| | AM : Moderate, Pearl (2 ba) to Light Ivory (2 ca) |
| | SP : Brown |
| Glycerol nitrate agar | G : Colorless, penetrating into medium |
| | R : Honey Gold (2 ic) to Mustard Gold (2 pg) |
| | AM : Moderate, Cream (1½ ca) |
| | SP : Pale yellowish brown |
| Glucose asparagine agar | G : Colorless, penetrating into medium |
| | R : Light Ivory (2 ca) to Chamois (2 gc) to Cinnamon (3 le) |
| | AM : Thin, white with a tinge of yellow, or moderate, cottony Shell (3 ca) to Pearl (3 ba) |
| | SP : None or very faint, yellowish brown |
| Glycerol asparagine agar | G : Chamois (2 gc) to Tan(3 ic), penetrating into medium |
| | R : Cinnamon (3 le) |
| | AM : Thin, white to Light Ivory (2 ca) or moderate, cottony, white with a tinge of pinkish yellow |
| | SP : Pale brown |
| Ca-malate agar | G : Cream (1½ ca), later Chamois (2 gc) |
| | R : Honey Gold (2 ic) to Cinnamon (3 le) |
| | AM : None or thin, Light Ivory(2 ca) |
| | SP : Pale brown |
| Inorganic salts starch agar | G : Colorless, penetrating into medium |
| | R : Cream (1½ ca) to Light Ivory (2 ca) |
| | AM : Abundant, cottony, white to Pearl (2 ba), later Pearl (3 ba) to Shell(3 ca) to Light Beige (3 ec) |
| | SP : Pale yellow |
| Yeast extract agar | G : Colorless, folded |
| | R : Honey Gold (2 ic) to Yellow Maple (3 ng) |
| | AM : Moderate, Dusty Yellow (1½ gc) or cottony, white to Pearl (3 ba) |
| | SP : Light Brown (3 lg) |
| Yeast malt agar | G : Good, colorless, penetrating into medium |
| | R : Light Ivory (2 ca) to Golden Brown (3pi) |
| | AM : Moderate, Light Ivory(2 ca) to Pastel Yellow (1 db) to Chamois (2 gc) or cottony, white to Pearl (3 ba) |
| | SP : Pale brown |
| Oatmeal agar | G : Good, colorless |
| | R : Yellow Maple (3 ng) |
| | AM : Abundant, cottony, White to Pearl (3 ba) to Light Beige (3 ec) |
| | SP : Pale yellowish brown |
| Potato plug | G : Maize (2 ga) to Chamois(2 gc) |
| | AM : Abundant, cottony, white to Pearl(3 ba) to Sand(3 cb), Partially Shell(3 ca) |
| | SP : Color of plug turns to grayish brown |
| Carrot plug | G : Good, Shell(3 ca) |
| | AM : Abundant, cottony, white to Pearl (3 ba) to Shell(3 ca) |

Table 1-continued

Cultural characteristics of Streptomyces rimofaciens No.B-98891 on various media

| Medium | *Characteristics |
|---|---|
| Nutrient agar | SP : Color of plug, scarcely changes |
| | G : Colorless |
| | R : Light Maize(2 ea) |
| | AM : Thin, white |
| | SP : Pale brown |
| Glucose nutrient agar | G : Good, colorless, folded |
| | R : Honey Gold(2 ic) to Topaz(3 ne) |
| | AM : Moderate, Pearl(3 ba) to Light Ivory(2 ca) |
| | SP : Pale brown |
| Glucose peptone gelatin | G : Surface growth good, colorless Growth in the medium, scant, colorless |
| | AM : Moderate, Cream (1½ ca) |
| | SP : Brown pigment, only arround the growth. After about 10 days incubation, bluish green pigment appeared near the surface, later changing to dark bluish green, and diffusing downward. Gelatin, not liquefied. |
| Skimmed milk | G : Surface, ring, Light Ivory (2 ca) to Light Maize(2 ea) |
| | AM : None |
| | SP : Maple (4 le), Coagulation and peptonization was observed. |

Abbreviations
G : Growth
R : Reverse
AM : Aerial mycelium
SP : Soluble pigment

3. Physiological properties
  1. Growth temperature range
    Growth occurs at 15°–38° C, better growth and formation of aerial mycelia is noted at 28°–36° C.
  2. Liquefaction of gelatin (cultivation at 24° C, 28 days):
    Not liquefied
  3. Hydrolysis of starch: Positive
  4. Reduction of nitrates:
    Negative; Bacto nitrate broth (ISP-No. 8: Method Manual of International Cooperative Project for Description and Deposition of Type Cultures of Streptomycetes, 1964) and Czapek's solution
  5. Coagulation of skimmed milk: Positive
    Peptonization of skimmed milk: Positive
  6. Production of melanoid pigment:
    Positive (peptone yeast iron agar) Negative (tyrosine agar)
  7. Assimilation of carbon sources (Method of Pridham and Gottlieb)
    Carbon sources well assimilated: inositol, D-galactose, D-glucose, maltose, D-mannose, starch, glycerine, sodium acetate, sodium succinate, sodium citrate.
    Carbon sources fairly assimilated: D-fructose, trehalose
    Carbon sources not assimilated: erythritol, adonitol, D-sorbitol, D-mannitol, dulcitol, D-xylose, L-arabinose, L-sorbose, rhamnose, melibiose, sucrose, lactose, raffinose, salicin, esculin, inulin.

As mentioned hereinbefore, the vegetative mycelium of this strain has a colorless to pale yellow surface, the reverse side being pale yellow to yellowish brown to brown. The aerial mycelium is either yellowish white or, in cottony part, yellowish orange to yellow with a tinge of gray. Light yellowish brown to brown soluble pigment is produced on certain synthetic agar. While the chromogenicity of this strain on proteinaceous media is weak, production of a blackish brown soluble pigment is clearly observed in peptone yeast iron agar, thus indicating that the strain is melaninpositive. On glucose peptone gelatin, a soluble brown pigment and a soluble bluish green pigment are produced.

Based on the cultural characteristics thus observed, the present strain was compared with the known species reported in the literature, such as S.A. Waksman, The Actinomycetes, II (The William and Wilkins Co., 1962), Cooperative Description of Type Cultures of Streptomyces II (International Journal of Systematic Bacteriology 18, p. 69), do III (ibid. 18, p. 279), do IV (ibids 19, p. 391), do V (ibid, 22, p. 265), Rocci et al, The Genus Streptoverticillium: A Taxonomic Study (Giornale di Microbiologia 17 p. 1, 1969) and others. As a result, it was found that the present strain was similar to Streptomyces rimofaciens (Japanese Patent Publication No. 7598/1967).

The differences between S. rimofaciens and the present strain are listed in Table 2. As for other characteristics not listed in the table, most of morphological, cultural and physiological properties of both strains are similar to each other.

The differences in the table are not sufficient to regard the present strain as a new species. However, in view of the fact that the present strain does not produce destomycin A and B but produces the present new antibiotic B-98891, we assume that this microorganism and Streptomyces rimofaciens are different strains and will hereinafter refer to it as Streptomyces rimofaciens No. B-98891. (IFO-13592, FERM-P No. 2549, ATCC-31120)

The numbers in the parentheses attached to the above-mentioned strain and indicated by IFO, FERM-P or ATCC are the accession numbers at Institute for Fermentation, Osaka, Japan (IFO); the Fermentation Research Institute of the Agency of Industrial Science and Technology, Chiba, Japan (FERM); and American Type Culture Collection, U.S.A. (ATCC), respectively.

Table 2

Comparison of S. sp. No.B-98891 with S. rimofaciens

| Medium | S. rimofaciens | S. sp. No.B-98891 |
|---|---|---|
| Bouillon agar and Glucose bouillon agar | Cracks formed in growth Soluble pigment Dark brown | No cracks Soluble pigment Pale brown |
| Carrot plug | No growth | Good growth with aerial mycelium |
| Assimilation of carbon sources | Sorbit and mannit are assimilated | Neither sorbit nor mannit assimilated |
| Antibiotic produced | Destomycin A & B | B-98891 |

As their common traits, Streptomyces are ready to undergo some cultural and physiological changes, and this applies to Streptomyces rimofaciens No. B-98891. Thus, the above-noted characters of the present strain are not constant but various mutants may be readily derived. Unless the antibiotic B-98891-producing ability is not lost, however, such mutants can be employed in the practice of this invention.

It does not matter, of course, whether such mutation has taken place spontaneously or been artificially induced by mutagenic treatment.

In the method of this invention, culture is carried out using a medium containing generally assimilable carbon sources, digestible nitrogen sources, inorganic salts and so on. In the medium, there may be incorporated, as required, trace nutrients, growth promoters, (e.g. vitamins, aminoacids, animal oil, vegetable oil, mineral oil), precursers and other materials which are effective in small amounts. The generally assimilable carbon sources include glucose, sucrose, molasses, starch, dextrin, glycerin, etc. and the digestible nitrogen sources include meat extract, soybean meal, corn steep liquor, peptone, casein, cotton seed meal, etc. as well as inorganic nitrogen compounds such as nitrates, ammonium compounds, etc. Other than these components, antifoaming agent and so on may be incorporated in the medium on demand. These materials can all be employed to advantage. While surface cultivation is feasible, aerobic submerged culture is more generally useful. In carrying out aerobic submerged culture, the pH of medium is preferably near neutral (i.e. pH 6.0–8.0) and the incubation temperature is preferably maintained around 20° to 37° C. These conditions of culture such as the composition and pH of medium, incubation temperature, severity of agitation or aeration, etc. may of course be controlled and selected so that they will provide satisfactory results, according to the particular strain of microorganism used, external conditions and other factors. Anyhow, the highest titre of the antibiotic B-98891 in the medium can generally be found 96 to 144 hours after the start of the cultivation.

The resultant culture broth contains a high titer of the antibiotic B-98891. To recover the antibiotic in optional purity from this broth, the separation procedures conventionally employed for recovering microbial metabolites from cultures can be utilized with advantage. For example, since, being a water-soluble base, the antibiotic B-98891, for the most part occurs in filtered broth, a filter aid is first added to the culture broth which is then filtered to remove the cells. The filtrate is then contacted with a suitable adsorbent to let the active fraction adsorbed and the latter is desorbed with a suitable solvent. Such a fractionation technique can be advantageously applied.

As said adsorbent, use can be made of activated carbon, adsorbent resin, cation exchange resins, activated alumina, silica gel and so on. In addition, use may also be made of a separation and purification procedure utilizing differences in molecular weight, such as one employing a molecular sieve. While the type of desorbing solvent depends upon the type and properties of the adsorbent, use may be suitably made of, for example, aqueous acetone, aqueous methanol, aqueous ethanol, aqueous propanol, aqueous butanol, etc. as well as acid, alkali, buffers and aqueous solutions of inorganic or organic salts.

More particularly, when the adsorbent is activated carbon or an adsorbent resin, the active substance in the filtered broth is adsorbed under neutral or weakly basic conditions and desorbed with water containing a suitable amount of acetone, methanol, propanol or the like, water containing a salt or acid, or a buffer solution, for instance.

Since the present antibiotic is a basic substance, it can be adsorbed on a cation exchange resin and eluted with a suitable acid, alkali or buffer solution. As said cation exchange resin, use may be made, for example, of Amberlite IRC-50 (manufactured by Rohm & Haas Company, U.S.A.) or Amberlite CG-50 (do). Thus, the antibiotic B-98891 can be adsorbed on a column of the resin and, then, eluted with dilute aqueous ammonia or a buffer solution, for instance. Aside from the above procedures, the antibiotic B-98891 may be purified by adsorption chromatography on silica gel (manufactured by Merck & Co., West Germany). Thus, the active eluate can be obtained by developing the chromatogram with a suitable solvent system such as a mixture of methanol, methylamine and water. It is also possible to accomplish the desired purification by adsorbing the present antibiotic on a support material having the property of a molecular sieve such as Sephadex G-15 (manufactured by Pharmacia, Sweden) and eluting the same, for example, with water or a buffer solution. The purification may also be accomplished by using such an adsorbent and a molecular sieve in a suitable combination.

The antibiotic B-98891 thus purified can then be obtained from methanol, acetone or the like as a colorless powder.

The following are the properties of the free antibiotic B-98891 powder obtained in Example 2 described hereinafter.

Figure 2:
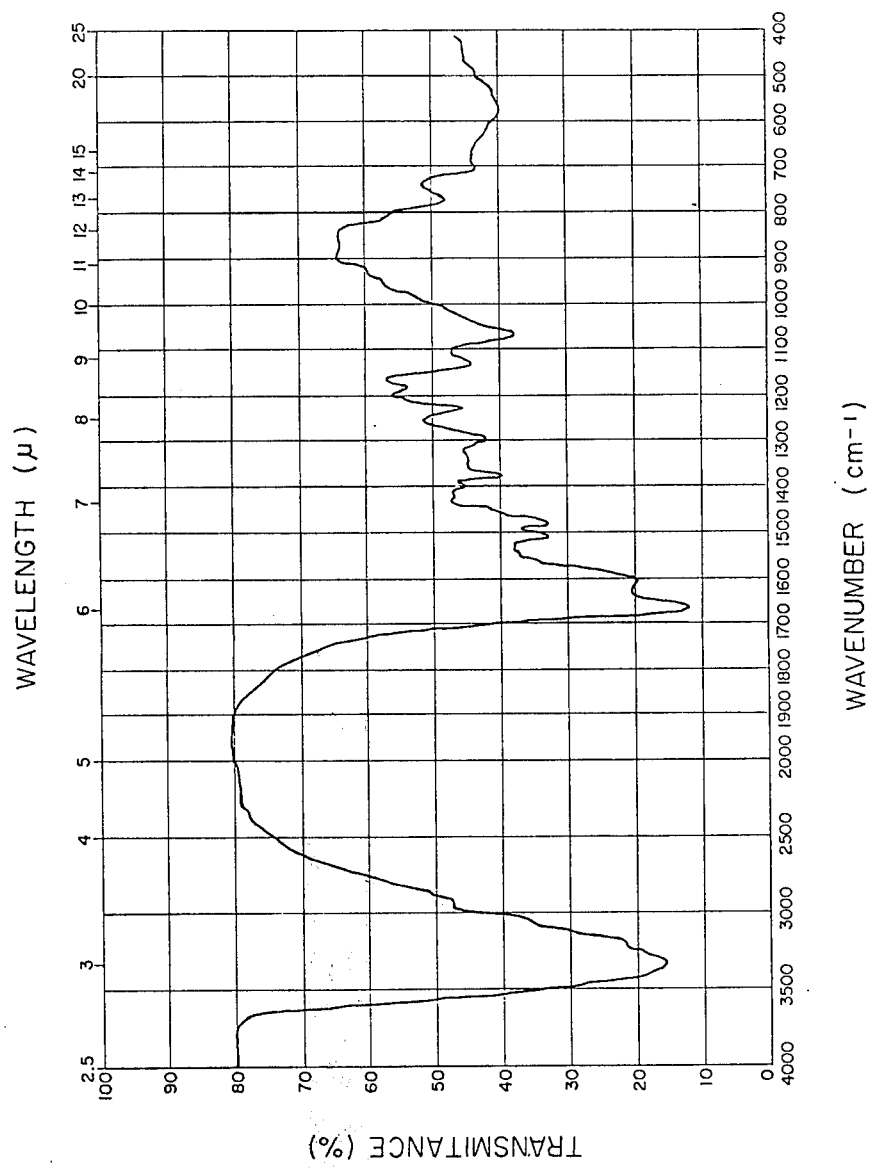

Physical and chemical properties
1. Melting point: Starts being gradually discolored at about 220° C, and does not show a definite melting point.
2. Specific rotation: $[\alpha]_D^{20}=+91.8°\pm10°(c=0.5$ in water); $+68.5°\pm10°(c=0.5, 1/10N$ HCl)
3. pKa: $4.2\pm0.2$, $7.0\pm0.2$(estimated by titration method)
4. Molecular weight: $529\pm100$(estimated by titration method)
5. Constituent elements and elemental analysis:
Composed of carbon, hydrogen, nitrogen and oxygen, and without halogen, phosphorus, sulfur.
C: $42.73\pm1.5$
H: $6.01\pm0.5$
N: $20.48\pm1.0$
O: $30.05\pm2.0$
6. Ultraviolet absorption spectra:
The Ultraviolet absorption spectra are shown in FIG. 1. In the diagram, the solid line represents the spectrum as measured in aqueous solution at pH 7; the dotted line the spectrum in 1/10N NaOH; and the broken line the spectrum in 1/10N HCl.
The absorption maxima are:
$\lambda_{max}^{pH\ 7}$ $271 \pm 2$ nm($E_{1\ cm}^{1\%}=157$)
$\lambda_{max}^{1/10N\ NaOH}$ $271 \pm 2$ nm($E_{1\ cm}^{1\%}=154$)
$\lambda_{max}^{1/10N\ HCl}$ $280 \pm 2$ nm($E_{1\ cm}^{1\%}=228$)
7. Infrared absorption spectrum
The infrared absorption spectrum as measured by the potassium bromide disc method is shown in FIG. 2. The significant absorptions (wave-numbers) are as follows.
3330, 3160(shoulder), 2900, 2850, 1660, 1600, 1505, 1485, 1400, 1375, 1295, 1230, 1180, 1130, 1065, 910, 780, 700, 580 cm$^{-1}$
8. Thin-layer chromatography (silica gel(Kiesal-Gel F$_{254}$, manufactured by Merck & Co., West Germany))

| Solvent system | Rf |
| --- | --- |
| Chloroform-methanol-17 % aqueous ammonia (2:2:1 - upper layer) | 0.34 |
| Propanol-pyridine-acetic acid-water (15:10:3:10) | 0.15 |
| Ethyl acetate-acetone-acetic acid-water | 0.37 |

| Solvent system | Rf |
| --- | --- |
| (45:5:5:45-lower layer) | |

9. Paper chromatography (Whatman No. 1 filter paper)

| Solvent system | Rf |
| --- | --- |
| Butanol-acetic acid-water (2:2:1) | 0.13 |
| Propanol-water (7:3) | 0.27 |
| Isopropanol-5 % aqueous ammonia (6:4) | 0.26 |

10. Paper electrophoresis (Whatman No. 1 filter paper, 500 V; completely migrated to the cathode side in 2 hours)

| Buffer solution | cm. |
| --- | --- |
| 1/10M glycine-NaCl-NaOH(pH 9.32) | −0.7 |
| 1/15M phosphate buffer (pH 7.05) | −1.1 |
| 1/10M citrate-HCl buffer(pH 3.62) | −3.3 |

11. Solubility

Easely soluble in water but only sparingly soluble in organic solvents (e.g. methanol, butanol, pyridine, acetic acid, dimethylsulfoxide, tetrahydrofuran)

12. Color reactions

Positive reactions to Greig-Leaback, Sakaguchi and potassium permanganate reagents; doubtful positive reactions to aniline phthalate and ninhydrin; negative reactions to Pauly, Ehrlich, Dragendorff, Barton, bentidine-periodate and ferric chloride-sulfosalicylic acid reagents.

12. Stability

Slightly unstable in the acidic aqueous solution but stable in neutral or basic aqueous solution.

Biological characteristics

1. Antimicrobial spectrum (in vitro)

The antimicrobial spectrum of the antibiotic B-98891 as measured by the agar dilution and diffusion methods is shown in Table 3. The "diameter of inhibition zone" in the table represents the diameter of the inhibition zone formed around a paper disc(7 mm. in diameter) immersed in a 5000 μg/ml. solution of the present antibiotic.

Table 3

| | Antimicrobial spectrum | | | | |
| --- | --- | --- | --- | --- | --- |
| Assay organism | Medium | Conductor of assay Temperature (° C) | Time | Minimal inhibitory concentration (μg/ml.) | Diameter of inhibition (mm) |
| Aspergillus niger IFO-4066 | A | 28 | 40 | >500 | + |
| Penicillium chrysogenum IFO-4626 | A | 28 | 40 | >500 | 13 |
| Penicillium expansum IFO-7813 | A | 28 | 40 | 100 | 25 |
| Pyricularia oryzae IFO-5279 | A | 28 | 40 | >500 | − |
| Cochliobolus miyabeanus IFO-5277 | A | 28 | 40 | >500 | 15 |
| Sclerotinia sclerotiorum IFO-9395 | A | 28 | 40 | 500 | 20 |
| Botrytis cinerea TKF-12 | A | 20 | 88 | 250 | 15 |
| Guignardia laricina IFO-7888 | A | 28 | 88 | 100 | 18 |
| Trichophyton mentagrophytes IFO-5809 | D | 28 | 88 | 500 | + |
| Candida albicans IFO-0583 | A | 28 | 40 | >500 | − |
| Saccharomyces cerevisiae IFO-0209 | A | 28 | 40 | >500 | 12 |
| Rhodotorula rubra IFO-0870 | A | 28 | 40 | 50 | 80 |
| Bacillus subtilis IFO-3513 | B | 37 | 20 | >500 | 14 |
| Staphylococcus aureus IFO-3061 | B | 37 | 20 | >500 | 10 |
| Escherichia coli IFO-3044 | B | 37 | 20 | 500 | 14 |
| Proteus vulgaris IFO-3045 | B | 37 | 20 | >500 | 11 |
| Pseudomonas aeruginosa IFO-3080 | B | 37 | 20 | >500 | − |
| Mycobacterium phlei IFO-3158 | C | 37 | 40 | 50 | 27 |
| Mycobacterium smegmatis ATCC-607 | C | 37 | 40 | 250 | 24 |

Assay media
A 3.0 % sucrose, 0.2 % L-asparagine, 0.3 % NH$_4$NO$_3$, 0.1 % KH$_2$PO$_4$, 0.1 % MgSO$_4$.7H$_2$O, 0.001 % versenol (manufactured by Dow Chemical Co.; an iron chelate compound; content of iron-sodium ethanol ethylene diamine triacetate is 57.04 %), 1.5 % agar (pH 7) Before use, the following vitamins are added to the medium to the indicated final concentrations.
1 μg/ml. thiamine, 1 μg/ml. riboflavin, 1 μg/ml. calcium pantothenate, 1 μg/ml. niacin, 0.005 μg/ml. biotin, 0.5 μg/ml. folic acid, 2 μg/ml. pyridoxine hydrochloride, 0.5 μg/ml. p-aminobenzoic acid, 0.0002 μg/ml. cyanocobalamin
B 0.5 % Ehrlich's meat extract, 0.5 % polypeptone, 0.5 % NaCl, 1.5 % agar (pH 7)
C 3.0 % glycerin, 0.5 % Ehrlich's meat extract, 0.5 % polypeptone, 0.5 % NaCl, 1.5 % agar (pH 7.0)
D 1.0 % glucose, 0.4 % (NH$_4$)$_2$HPO$_4$, 0.07 % MgSO$_4$.7H$_2$O, 0.1 % KH$_2$PO$_4$, 0.1 % NaCl, 0.003 % FeSO$_4$, 1.5 % agar (pH 7.0)

Assay media

A 3.0% sucrose, 0.2% L-asparagine, 0.3% NH$_4$NO$_3$, 0.1% KH$_2$PO$_4$, 0.1% MgSO$_4$.7H$_2$O, 0.001% versenol (manufactured by Dow Chemical Co.; an iron chelate compound; content of iron-sodium ethanol ethylene diamine triacetate is 57.04%), 1.5% agar (pH 7) Before use, the following vitamins are added to the medium to the indicated final concentrations. 1 μg/ml. thiamine, 1 μg/ml. riboflavin, 1 μg/ml. calcium pantothenate, 1 μg/ml. niacin, 0.005 μg/ml. biotin, 0.5 μg/ml. folic acid, 2 μg/ml. pyridoxine hydrochloride, 0.5 μg/ml. p-aminobenzoic acid, 0.0002 μg/ml. cyanocobalamin B 0.5% Ehrlich's meat extract, 0.5% polypeptone, 0.5% NaCl, 1.5% agar (pH 7)
C 3.0% glycerin, 0.5% Ehrlich's meat extract, 0.5% polypeptone, 0.5% NaCl, 1.5% agar (pH 7.0)
1.0% glucose, 0.4% $(NH_4)_2HPO_4$, 0.07% $MgSO_4.7H_2O$, 0.1% $KH_2PO_4$, 0.1% NaCl, 0.003% $FeSO_4$, 1.5% agar (pH 7.0)

It is apparent from Table 3 that the antibiotic B-98891 is weakly active against certain gram-positive bacteria, gram-negative bacteria, phytopathogenic fungi and certain yeasts.

The microbial assay of the antibiotic B-98891 was conducted by the diffusion method using potato sucrose agar (3% sucrose, pH 5) as an assay medium and *Rhodotorula rubra* IFO-0907 as an test organism.

2. The activity against the powdery mildew of barley.

The seven days stage seedlings of barley were used and their roots were covered with small cotton wool wetted with a predetermined concentration of the antibiotic B-98891. The unfolded leaves were inoculated with conidia of *Erysiphe graminis* using a small brush and each stock was kept in a test tube at 18° C for 7 days. The percent area of the resultant lesion was calculated to determine the effect of the test drug. The result is set forth in Table 4.

Table 4

| Test compound | Activity against powdery mildew of barley | |
|---|---|---|
| | Concentration | Percent area of lesion |
| B-98891 | 50 ppm | 0 % |
| | 25 | 0 |
| | 12.5 | 0 |
| | 6.25 | 26 |
| | 3.12 | 40 |
| Benomyl wettable powder* | 62.5** | 14 |
| Control(untreated) | — | 100 |

*An agricultural chemical containing methyl-1-(butylcarbamoyl)-2-benzimidazole carbamate as an active ingredient
**Concentration as methyl-1-(butylcarbamoyl)-2-benzimidazole carbamate It is thus apparent that the antibiotic B-98891 has a more potent onset control activity than the commercially available chemical.

3. Toxicity

The acute toxicities in mice and rats are as follows.

| Route of administration | $LD_{50}$ (mg/kg.) | |
|---|---|---|
| Animal species | Intravenous | Oral |
| Mice | >500 | >2000 |
| Rats | >500 | >2000 |

As for the action of the drug upon the rabbit's cornea and skin, no change was noted during 10 days of observation at the concentration level of 1000 ppm.

In a fish toxicity test, no toxic effect against Japanese killifish was observed at a concentration of 20 ppm during 7 days observation.

Comparison with known antibiotics

The foregoing properties show that the antibiotic B-98891 is a nucleoside antibiotic. Among the known antibiotics of this type, gougerotin, anthelmycin, blasticidin S, aspiculamycin, hikijimycin, moroyamycin A,B (gougerotin analogs) & C, cytovirin, are somewhat similar to the antibiotic B-98891 in ultraviolet absorption spectrum.

However, the ultraviolet absorption spectra of these known antibiotics all show absorption maxima at 268 nm (in alkaline aqueous solution) and 276 nm(in acidic aqueous solution), whereas the antibiotic B-98891 shows the maxima at 271±2nm (in alkaline aqueous solution) and 280±2nm(in acidic aqueous solution). Moreover, of said known antibiotics, all the compounds whose chemical structures have been elucidated have cytosine as a chromophore, but the chromophore of the antibiotic B-98891 has been determined to be 5-hydroxymethyl cytosine. From the above results, the antibiotic B-98891 is certainly considered to be a new antibiotic.

As its biological properties indicate, this new antibiotic B-98891 is weakly active against gram-positive and gram-negative bacteria.

Its toxicity in mice and rats is also mild, and substantially no stimulant action is found on the cornea and skin in rabbits. Thus, this is considered to be a sparingly toxic antibiotic.

On the other hand, the present antibiotic has a characteristically high activity against the causative agent of powdery mildew of barley (*Erysiphe graminis*) and, in addition, has a highly beneficial feature that it is substantially harmless to fish.

Powdery mildew is wide-spread and the existing control agents for powdery mildew have been attended by various problems such as effectiveness (including the problem of resistance), injury to the plant, residues, the nuisance problems associated with their production, and so on. The present antibiotic contributes a great deal to the solution of these problems.

In the plant fungicidal composition of this invention is contained antibiotic B-98891 as an active ingredient.

The antibiotic B-98891 may be employed either alone or in combination with other chemicals known to be applicable to plants. As the antibiotic B-98891, culture broth itself or any concentrate containing the antibiotic B-98891 whose contents are over about 50% in purity may also be employed. Such a concentrate means filtrate, condensate of the filtrate, or any material obtainable as intermediate of the purification, inclusively.

As for the application forms, any of the forms in which conventional fungicides are usually employed can be utilized. For example, the antibiotic is dissolved or dispersed in a liquid vehicle (e.g. a solvent), or admixed with or adsorbed on, a suitable carrier (e.g. diluent, excipient, etc.). If necessary, an emulsifier, dispersing agent, suspending agent, spreader, peneration aid, wetting agent, viscosity builder, stabilizer and other additives may be further incorporated in the preparations so that the composition may be put to use in such application forms as oily solutions, emulsions, wettable powders, dusts, tablets, granules, aerosol sprays and so on.

In such forms as emulsions and wettable powders, the concentration of the principal active ingredient is preferably in the range of about 1 to 70 percent by weight; as oils, dusts and other forms, the preferred concentration range is from about 0.01 to 10 percent by weight. In the case of emulsions and wettable powders, the composition is diluted or adulterated to a suitable concentration (e.g. 100 to 10000-fold) with water or other diluent before application.

Suitable examples of the aforementioned solvent used in the composition of this invention are water, alcohols (e.g. methanol, ethanol, ethylene glycol, etc.), ethers (e.g. dioxane, tetrahydrofuran, cellosolve, etc.), aliphatic hydrocarbons (e.g. gasoline, kerosene, fuel oil, machine oil, etc.), aromatic hydrocarbons (e.g. benzene, toluene, xylene, solvent naphtha, methylnaphthalene, etc.), organic bases (e.g. pyridine, aldehyde-collidine, etc.), halogenated hydrocarbons (e.g. chloroform, carbon tetrachloride, etc.), acid amides (e.g. dimethylformamide, etc.), esters (e.g. ethyl acetate, butyl acetate, fatty acid glyceride esters, etc.), and nitriles (e.g. acetonitrile, etc.). These solvents may be employed alone or in combination.

As the diluent or/and excipient, there may be mentioned vegetable powders (e.g. soybean meal, tobacco flour, wheat flour, saw dust, etc.), mineral powders (e.g. kaolin, bentonite, acid clay and other clay minerals, talcum powder, pagodite and other talcs, diatomaceus earth, mica powder and other silicas), alumina, sulfur powder, activated carbon and so on. These materials may be employed alone or in combination.

As the surface active agents used as said emulsifier, spreader, penetration aid, dispersing agent and so on, there may as required be employed various soaps, sulfuric acid esters of higher alcohols, alkylsulfonic acids, alkylarylsulfonic acids, quaternary ammonium salts, oxyalkylamines, fatty acid esters, polyalkylene oxide surfactants, anhydrosorbitol surfactants and so on. For the same purposes, casein, gelatin, starch, alginic acid, agar, polyvinyl alcohols, wood terpentine oil, rice bran oil, bentonite, cresol soap, etc. may also be employed.

The composition thus obtained may be further supplemented with other types of fungicides and disinfectants (e.g. copper-type fungicides, mercurial fungicides, organic sulfur fungicides, phenol-type fungicides, etc.), herbicides, insecticides (organic chlorine insecticides, organophosphorus insecticides, natural insecticides, etc.), other miticides, nematocides, plant growth regulators, synergists, attractants, repellents, perfumes, plant nutrients, fertilizers and so on.

The proper amount of the plant fungicidal composition of this invention, the types of other chemicals to be mixed with the present composition and the proportionate amounts of such active ingredients in the final composition, for instance, depend upon the variety of the crop plant to which the composition is to be applied, the growth stage and condition of the crop plant, the method of growing the plant, the type of disease, the condition of onset, the time at which the composition is applied and certain external environmental factors, the method or route of application, the economics of application and other conditions. Usually, however, it is sufficient to apply at the rate of about 1 to 300 grams in terms of the compound of this invention to every 10 ares. As for the effective concentration, it is desirable that the final concentration of the compound of this invention is in the range of 1 μg/ml. to 10 mg/ml. In use, the fungicidal composition of this invention can be applied directly to the aerial part of the crop plant or to the soil.

Thus, the invention is not limited in whatever manner by the amount or method of application, but all that is necessary is to ensure that the composition will be applied safely and effectively to crop plants.

The plant fungicidal composition of this invention is active against various diseases in plants and, in addition, has miticidal activity. For example, the composition is particularly effective against powdery mildew of edible crop (e.g. barley), industrial crop (e.g. tobacco and Japanese mulberry), fruit trees (e.g. apple and grape), forest crop (e.g. oak), vegetables (e.g. cucumber, oriental melon, pepper, tomato, garden pea and strawberry), ornamental plants (e.g. rose) and so on, as well as late blights of tomato, potato and other plants. The present composition is substantially nontoxic (e.g. acute toxicity, stimulant action on the cornea and skin, toxicity in fish, etc.) and is extremely safe to use.

The following are some test data and examples showing the beneficial effects of this invention in comparison with various chemicals which are commercially available as controlling chemicals for the respective plant diseases mentioned heretofore.

These various chemicals used as the control in the test are commercial products, the active ingredients of which are as set forth below. The concentrations in the tables refer to the concentrations of such active ingredients.

| | |
|---|---|
| Karathane EM (distributed by Sanyo Boeki Co.,Japan) dinitromethylheptylphenyl crotonate | 37 % |
| Takeda-Mycin Conc.(manufactured by Takeda Chemical Industries, Ltd.) dihydrostreptomycn sulfate | 12.5 % |
| Benlate WP (manufactured by du Pont, U.S.A.) methyl-1-(butylcarbamoyl)-2-benzimidazole carbamate | 50 % |
| Polyoxin AL WP (distributed by Kumiai Chemical Co.,Japan) as polyoxine complex B | 10 % |
| Morestan WP (distributed by Nihon Tokushunoyaku Co.,Japan) 6-methylquinoxaline 2,3-dithiocarbonate | 25 % |

TEST EXAMPLE 1

The control test of powdery mildew of oriental melon. The unfolded leaves of oriental melon plants (*Cucumis melo* L. var. *makuwa* Makino, f. *Ginsen*) grown in pots (6 to 7-leaf stage) were inoculated with *Sphaerotheca fuliginea* (Schlechtendahl) Pollacci by dusting the spores of the fungi off the diseased leaves.

The antibiotic B-98891 was diluted with water to a predetermined concentration and a spreader ("Dyne" manufactured by Takeda Chemical Industries, Ltd.) was added in a sufficient amount to give a final 3000-fold dilution. The control chemical was also similarly diluted with water.

Each of these fungicidal solutions was sprayed in adequate volume to the above oriental melon plants two days after the inoculation. Then, the plants were further grown and cared in the routine manner in a green-house. At timed intervals, the percent area of fungal growth on the leaves that had already been unfolded at the time of spraying was determined. This test was conducted in duplicate per group.

Table 5

The controlling effect of antibiotic B-98891 against powdery mildew of oriental melon

| Test substance | Concentration (ppm) | Percent area of the lesion (%) | | | Phytotoxicity |
|---|---|---|---|---|---|
| | | 7 days | 14 days | 21 days | |
| B-98891 | 40 | 0 | 19.0 | 40.0 | — |
| | 80 | 1.5 | 7.0 | 24.0 | — |
| | 160 | 0.6 | 0.6 | 5.0 | — |
| Karathane EM | 148 | 0.5 | 5.0 | 14.5 | — |
| Control (untreated) | — | 65.0 | 97.0 | 100 | — |

TEST EXAMPLE 2

The control test of powdery mildew of pepper

The reverse sides of unfolded leaves of pot-grown pepper plants (9 to 10-leaf stage, *Capsicum annuum L. f. California Wonder*) were inoculated, by dusting, with the pathogenic fungi from infected leaves. Two days later, the leaves were sprayed with adequate volume of test solutions as in Test Example 1. Then, the plants were grown and cared in a green-house and, after timed intervals, the percent area of fungal growth was determined. This test was performed in duplicate for each group.

Table 6

The effect of antibiotic B-98891 against powdery mildew of pepper

| Test substance | Concentration (ppm) | Percent area of the lesion (%) 7 days | 10 days | Phytotoxicity |
|---|---|---|---|---|
| B-98891 | 80 | 7.9 | 10.3 | — |
|  | 160 | 5.0 | 4.6 | — |
| Karathane EM | 148 | 7.2 | 18.1 | — |
| Control (untreated) | — | 24.6 | 76.2 | — |

TEST EXAMPLE 3

The control test of late blight of tomato

Tomato plants (*Lycopersicon esculentum* Mill, *f. Ohgata Fukuju*) which were grown in 12 cm pots for 30 days were used in the test. The test was carried out in duplicate per group of 4 pots. The fungicidal solutions prepared in the same manner as Test Example 1 were sprayed in adequate volume and, two days later, a suspension of the spores of *Phytophthora infestans* (Montagne) de Bary was further sprayed over the plants. The pots were kept in a green-house for 4 days and, then, the percent area of the lesions (on the third and fourth leaves) was determined.

Table 7

The effect of antibiotic B-98891 against late blight of tomato

| Test substance | Concentration (ppm) | Percent area of lesions (%) | Degree of sporulation | Phytotoxicity |
|---|---|---|---|---|
| B-98891 | 250 | 100 | Moderate | — |
|  | 500 | 0 | None | — |
| Takeda-Mycin Conc. | 500 | 28 | Scanty | — |
| Control (untreated) | — | 100 | Good | — |

TEST EXAMPLE 4

The control test of powdery mildew of barley

Five- or six-leaf barley seedlings (*Hordeum vulgare* L. *f. Shiga Hakkoku* No. 5) in pots were grown in a box equipped with illuminating lamps (Plant-Lux[R], manufactured by Tokyo Shibaura Electric Co. Ltd., Japan) at 20° C. The pots were placed adjacent to the pots of diseased barley plants so that the seedlings acquired the disease. The fungicidal solutions prepared in the same manner as Test Example 1 were sprayed over the seedlings in adequate volume at intervals of 10 days and, after the third application, the plants were further grown and cared in the above manner till the 10th day. To ascertain the degree of onset of the disease, the percent area of lesions was investigated in conformity with the Japanese official criteria for the percent area of powdery mildew lesions in wheat, oat, barley and rye (provided by The Bureau of Agricultural Administration, the Ministry of Agriculture and Forestry, Japan).

Table 8

The effect of antibiotic B-98891 against powdery mildew of barley
Percent area of lesions (%)

| Test substance | Concentration (ppm) | 6th leaf Day of investigation A | B | C | 9th leaf Day of investigation B | C |
|---|---|---|---|---|---|---|
| B-98891 | 15.6 | 0.4 | 2.1 | 0.8 | 2.3 | 10.5 |
|  | 31.2 | 0.3 | 2.0 | 1.3 | 0.3 | 1.3 |
|  | 62.5 | 0.1 | 0.1 | 0 | 0.5 | 0.4 |
| Benlate WP | 125 | 0.3 | 0.4 | 0.2 | 1.3 | 1.6 |
| Control (untreated) | — | 8.4 | 100 | Blight | 68.5 | Blight |

Day of investigation:
A – 10 days after first application
B – 10 days after second application
C – 10 days after third application
The first application was carried out on the six-leaf stage.

TEST EXAMPLE 5

The control test of powdery mildew of tobacco plant

Tobacco plants (*Nicotiana tabacum* L. *f. MC*) grown in pots, with the fourth mature leaf sufficiently unfolded, were prepared in a green-house, two pots per group, for this test. To encourage the onset of the disease, the pots of diseased plants were placed next to the test pots for spontaneous infection. The fungicidal solutions were prepared in the same manner as Test Example 1 and sprayed onto the test plants in two divided doses, each in sufficient volume, at intervals of 10 days. The percent area of the lesion was investigated 9 days and 15 days, respectively, after the last application.

Table 9

The effect of antibiotic B-98891 against the powdery mildew of tobacco plant

| Test substance | Concentration (ppm) | Percent area of lesion (%) 9 days | 15 days | Phytotoxicity |
|---|---|---|---|---|
| B-98891 | 40 | 11.6 | 20.4 | — |
|  | 80 | 10.0 | 13.2 | — |
|  | 160 | 6.0 | 8.5 | — |
| Polyoxin AL WP | 160 | 61.5 | 90.0 | — |
| Control (untreated) | — | 95.0 | 100 |  |

TEST EXAMPLE 6

The control test of the powdery mildew of rose

For this test, rose (*Rosa spp.*) plants were grown in pots at a green-house. As test plants (forma species: Super Star and Arlene Francis) were used in groups of 3 pots per treatment. The fungicidal solutions prepared in the same manner as Test Example 1 were sprayed in sufficient volume, at intervals of 7 days and the plants were kept under the same condition until the spontaneous onset of the disease took place. The number of diseased leaflets on three branches per pot was investigated 7 days after the third application and the percentage of diseased leaflets relative to the total number of leaflets investigated was calculated.

Table 10

The effect of antibiotic B-98891 against powdery mildew of rose

| Test substance | Concentration (ppm) | Percent of diseased leaflet (%) Super Star | Phytotoxicity | Arlene Francis | Phytotoxicity |
| --- | --- | --- | --- | --- | --- |
| B-98891 | 40 | 5.6 | — | 14.9 | — |
|  | 80 | 3.2 | — | 6.7 | — |
|  | 160 | 2.6 | — | 2.2 | — |
| Karathane EM | 148 | 52.8 | — | 52.9 | — |
| Control (untreated) | — | 100 | | 88.8 | |

TEST EXAMPLE 7

The control test of powdery mildew of apple plant

The seedlings of the apple (*Malus pumila* Miller *var. domestica* Schneider *f. Rall's Janet*) in their 5- to 8-leaf stage were employed. The pathogenic fungi on diseased leaves of an apple plant were dusted over the tops of the seedlings which, then, were kept in a green-house. After 2 days, the fungicidal solutions prepared in the same manner as Test Example 1 were sprayed in sufficient volume. After the application, the seedlings were further grown in a green-house. After 12 days, the percent area of the lesion was investigated. The test was conducted in hexaplicate for each group.

Table 11

The effect of antibiotic B-98891 against the powdery mildew of apple plant

| Test substance | Concentration (ppm) | Percent area of the lesion (%) 12 days | Phytotoxicity |
| --- | --- | --- | --- |
| B-98891 | 40 | 0.9 | — |
|  | 80 | 0.6 | — |
|  | 160 | 0 | — |
| Karathane EM | 148 | 0.9 | — |
| Control (untreated) | — | 27.9 | — |

TEST EXAMPLE 8

The control test of powdery mildew of oak tree

This test was conducted with shoots of naturally grown oak (*Quercus glauca* Thunb.) trees about 10 years old. The fungicidal solutions prepared in the same manner as Test Example 1 were applied in mists.

The old mature leaves had already been severely diseased and, therefore, spontaneous infection of young leaves on the shoots was expected.

The number of treated leaves was 50 per group. The percent area of the lesion on treated leaves was investigated at 7 days after the treatment.

Table 12

The effect of antibiotic B-98891 against the powdery mildew of oak tree.

| Test substance | Concentration (ppm) | Percent area of lesion (%) 7 days | 14 days | Phytotoxicity |
| --- | --- | --- | --- | --- |
| B-98891 | 40 | 8.3 | 26.4 | — |
|  | 80 | 1.1 | 1.5 | — |
|  | 160 | 0.6 | 0.5 | — |
| Karathane EM | 148 | 1.8 | 3.4 | — |
| Morestan WP | 83 | 7.5 | 22.1 | — |
| Control (untreated) | — | 16.7 | 35.8 | — |

TEST EXAMPLE 9

The control effect against drug-resistant strain

The leaves of a cucumber plant (*Cucumis sativus L. f. Suyo*) infected with powdery mildew were flipped over a 1-month cucumber plant in a pot so that the latter was inoculated with *Sphaerotheca fuliginea* Pollacci. After 1 day, the fungicidal solutions prepared in the same manner as Test Example 1 were sprayed in sufficient volume over the plant. After about 14 days, the fungal growth formed were used to further inoculate intact cucumber plants. One day after the inoculation, fungicidal solution was sprayed and, after 7 days, the percent area of the lesion was determined.

Table 13

The effect of antibiotic B-98891 against a drug-resistant powdery mildew

| History of inoculum | Percent area of lesion Benlate WP 250 ppm | B-98891 40 ppm | Control (untreated) |
| --- | --- | --- | --- |
| Lesions after application of Benlate WP (250 ppm) | 78.3 | 21.7 | 100 |
| Lesions after application of B-98891 (80ppm) | 0.8 | 18.3 | 66.7 |
| Control (untreated) | 5.0 | 15.8 | 76.7 |

TEST EXAMPLE 10

The control test of powdery mildew of strawberry

The fungicidal solutions prepared in the same manner as Test Example 1 was sprayed over strawberry (var. Hogyoku) at the stage of flowering, grown at a green house, in adequate volume at intervals of 7 days. The percent area of the lesions was determined 7 days after the second application. In the group to which the composition of this invention was applied at the concentration of 20 ppm, a remarkable effect was observed in comparison with the control group. The effect was found to be superior to those by applying Morestan WP at the concentration of 80 ppm and by applying polyoxin AL WP at the concentration of 100 ppm to the test plants in the same manner as above.

It was further made clear that the composition of this invention showed superior control effects against the powdery mildew of garden pea, grape and other plant.

The following examples are further illustrative of the present invention. It should be understood, however, that the invention is by no means limited by the particular examples.

In these Examples, the terms "part(s)" means "weight part(s)" unless otherwise specified, and the relationship between "part(s)" and "part(s) by volume" corresponds to that between gram(s) and milliliter(s).

EXAMPLE 1

A Sakaguchi flask of 3 liters capacity was charged with 500 milliliters of a medium composed of 1.0% of glucose, 0.3% of yeast extract and 0.5% of Bacto-tryptone (Pancreatic digest of casein used as a nutrient in microbiology, manufactured by Difco Laboratories, U.S.A.) (pH 7) and, then, sterilized. The flask was then inoculated with a loopful of *Streptomyces rimofaciens* No. B-98891 (ATCC 31120) from a slant culture and incubated on a reciprocating shaker (120 reciprocating strokes/min.) at 28° C for 48 hours. Separately, a stainless steel tank with a capacity of 50 liters was charged with 30 liters of a medium composed of 3.0% of glucose, 2.2% of soybean flour, 0.3 of polypeptone, 0.4% of precipitated calcium carbonate and 0.05% of an antifoaming agent ("Antifroth F 102"=manufactured by Daiichi Kogyo Seiyaku K.K., Japan), after sterilization, the medium was inoculated with the entire amount (500 milliliters) of the previously obtained culture from the Sakaguchi flask.

Aerated submerged culture was carried out under sparging at 30 liters/min. and at 100 r.p.m. and 28° C for 48 hours to obtain a seed culture.

A stainless steel tank with a capacity of 200 liters was charged with 100 liters of a medium of the same composition as that used in the above-mentioned tank culture and, after sterilization, 10 liters of the above seed culture was added. Aerated submerged culture was carried out under sparging at 50 liters/min. and at 100 r.p.m. and 28° C for 114 hours.

To 80 liters of the culture broth thus obtained was added 1.6 kilograms of a filter aid, ("Hyflo-supercel" manufactured by Johnes-Manville, U.S.A.), followed by filtration to obtain 60 liters of a filtrate.

The filtrate thus obtained was effective against *Erysiphe graminis* in a concentration of 32 times dilution.

As to the manner of this test, reference is made to the description on page 19.

The above filtrate was adjusted to pH 8 and passed through a column packed with 7 liters of ion exchange resin Amberlite IRC-50 (manufactured by Rohm & Haas Company, U.S.A.).

The column was washed with 40 liters of water and, then, with 40 liters of 0.5% aqueous ammonia. Then, the active component was eluted with 40 liters of 2% aqueous ammonia. The resultant eluate was passed through a column packed with 3 liters of chromatographic activated carbon (manufactured by Takeda Chemical Industries, Ltd., Japan), which was then washed with 20 liters of water and, then, with 20 liters of 5% acetone. The active component was eluted with 15 liters of 30% acetone and 15 liters of 50% acetone. The active fractions were pooled and concentrated. Upon addition of 0.5 liters of methanol, there is obtained 38 g. of a brown-colored crude powder.

The crude powder thus obtained inhibited completely the growth of *Erysiphe graminis* at a concentration of 25–50 ppm.

As to the manner of this test, reference is made to the description on page 19.

The above crude powder was dissolved in water and the aqueous solution was passed through a column packed with 35 liters of ion exchange resin Amberlite CG-50 (manufactured by Rohm & Haas Company, U.S.A.). The column was washed with 2.5 liters of water and, then, with 1.5 liters of 0.5% aqueous ammonia. The active component was then eluted with 1.5 liters of pyridine-acetic acid-water (2:1:97) buffer and, then, with 1.5 liters of pyridine-acetic acid-water (4:2:94) buffer. The resultant eluate was concentrated and methanol was added to the concentrate. The procedure provided B-98891 acetate (16 g.) as a colorless powder.

EXAMPLE 2

In a stainless steel tank with a capacity of 200 liters was prepared 100 liters of a medium (pH 7) composed of 3.0% of glucose, 2.2% of soybean flour, 0.3% of polypeptone, 0.4% of precipitated calcium carbonate and 0.05% of an antifoaming agent ("Antifroth F 102" manufactured by Daiichi Kogyo Seiyaku, K.K., Japan) and, after sterilization, the medium was inoculated with the entire amount of a culture in a Sakaguchi flask prepared in the same manner as Example 1. Submerged culture was carried out under sparging at 50 liters/min. and at 100 r.p.m. and 28° C for 48 hours to prepare a seed culture.

In a stainless steel tank with a capacity of 2000 liters was prepared 1000 liters of a medium (pH 7) composed of 5.0% of glucose, 3.5% of soybean flour, 1.0% of Pharmamedia (a cottonseed-derived protein nutrient used in microbiology, manufactured by Traders' Oil Mill Company, U.S.A.), 0.5% of NaCl and 0.5% of precipitated calcium carbonate. After sterilization, 100 liters of the above seed culture was added and submerged culture was carried out under sparging at 500 liters/min. and at 100 r.p.m. and 28° C for 114 hours.

The culture broth thus obtained was treated in the same manner as Example 1 to obtain 750 liters of a filtrate.

This filtrate yielded 225 g. of a crude powder.

The above crude powder was dissolved in water and the aqueous solution was passed through a column packed with 5 liters of ion exchange resin Amberlite CG-50 (manufactured by Rohm & Haas Company, U.S.A.). The column was washed with 25 liters of water and, then, with 25 liters of 0.5% aqueous ammonia, followed by elution with 17 liters of 1% aqueous ammonia. The resultant eluate was then passed through a column of 10 liters of chromatographic activated carbon pretreated with 2% aqueous ammonia. The column was washed with 50 liters of 2% aqueous ammonia and, then, with 50 liters of 5% acetone-2% aqueous ammonia, followed by washing with 50 liters of 5% acetone. Then, elution was carried out with 80 liters of 20% acetone and the resultant eluate was concentrated. Methanol was added to the concentrate, whereby the free B-98891 was obtained as colorless powder (150 g.).

EXAMPLE 3

A crude powder was obtained from 700 liters of a filtered broth prepared by the same cultivation and filtration procedures as described in Example 2. The crude powder was dissolved in water and the aqueous solution was purified by means of ion exchange resin Amberlite CG-50 (manufactured by Rohm & Haas Company, U.S.A.). The product was further passed through a column of 5 liters of chromatographic activated carbon. The column was washed with 25 liters of water and, then, with 25 liters of 5% acetone. The active substance was then eluted with 35 liters of 20% acetone-0.5% formic acid and the resultant eluate was concentrated. Methanol was added to the concentrate, whereby B-98891 formate was obtained as a colorless powder (115 g.). The properties of this formate are as follows.

Melting point: 228° C (decomp.)

$[\alpha]_D^{25} +88.4° \pm 10°$ ($c=0.5$ in water) $+66.9° \pm 10°$ ($c=0.5$ in 1/10N HCl)

$UV\lambda_{max}$: nm($E_{1\ cm}^{1\%}$)

pH 7: 271 (142)

1/10N NaOH: 271 (139)

1/10N HCl: 280 (210)

Elemental analysis

C, 40.50±1.5; H, 5.77±0.5; N, 18.55±1.0

The corresponding hydrochloride was obtained by elution with 20% acetone-1/20N hydrochloric acid instead of 20% acetone-0.5% formic acid. The properties of this hydrochloride are as follows.

Melting point: 224° C (decomp.)
$[\alpha]_D^{25}$ +81.3°±10° (c=0.5, in water) +63.3°±10° (c=0.5, in 1/10N HCl)
UV$\lambda_{max}$: nm ($E_{1\,cm}^{1\%}$)
pH 7: 272 (142)
1/10N NaOH: 272 (147)
1/10N HCl: 280 (213)
Elemental analysis
C, 38.81±1.5; H, 5.75±0.5; N, 18.25±1.0

The biological activity of these salts was substantially equal to that of free B-98891.

EXAMPLE 4

A wettable powder was prepared by compounding 10 parts of antibiotic B-98891, 2 parts of sodium ligninsulfonate, 3 parts of polyoxyethylene-alkylaryl-ether and 85 parts of clay. This powder is diluted 500 to 1000 times with water and the dilution is sprayed evenly over farm or horticultural crop plants at a rate of 100 to 200 liters per 10 ares.

EXAMPLE 5

A dust was prepared by mixing 0.5 part of antibiotic B-98891 and 99.5 parts of clay. This product is directly applied at a rate of 3 to 5 kilograms per 10 ares.

EXAMPLE 6

A water-soluble preparation was prepared by compounding 10 parts of antibiotic B-98891, 5 parts of polyoxyethylenealkylaryl-ether and 85 parts of lactose, with stirring. The preparation is diluted to a suitable concentration with water and evenly sprayed over farm crop and horticultural plants at the rate of 100 liters per 10 ares.

EXAMPLE 7

An aqueous solution was prepared by mixing 50 parts of antibiotic B-98891, 5 parts of methanol, 5 parts of amine stearate and 40 parts of water. The solution is diluted with water and sprayed in the same manner as Example 4.

EXAMPLE 8

A granular product was prepared by mixing 0.5 part of antibiotic B-98891, 5 parts of gum Arabic, 30 parts of bentonite and 64.5 parts of talc and granulating the resultant mixture. The product is directly applied at the rate of 3 to 5 kilograms per 10 ares.

Just as did the product used in the test examples given hereinbefore, the compositions described in the above working examples displayed outstandingly superior effects as pest control agents against powdery mildew of barley, rose and tobacco, Benlate-resistant powdery mildew of cucumber, late blight of tomato and other crop pests.

What we claim is:

1. A member selected from the group consisting of antibiotic B-98891 and the acid addition salts thereof, wherein the antibiotic has the following properties:
  a. Melting point: Starts being gradually discolored at about 220° C, and does not show a definite melting point.
  b. Elemental analysis: C, 42.73±1.5%; H, 6.01±0.5%; N, 20.48±1.0%; O, 30.05±2.0%,
  c. The molecular weight estimated by titration method is 529±100,
  d. Specific rotation: $[\alpha]_D^{20}$ = 91.8°±10° (c=0.5, H$_2$O); 68.5°±10° (c=0.5, 1/10N HCl)
  e. pKa: 4.2±0.2, 7.0±0.2 (titration)
  f. Ultraviolet absorption spectrum:
  $\lambda_{max}^{pH\,7}$ 271±2 nm ($E_{1cm}^{1\%}$ = 157)
  $\lambda_{max}^{1/10N\,NaOH}$ 271±2 nm ($E_{1cm}^{1\%}$ = 154)
  $\lambda_{max}^{1/10N\,HCl}$ 280±2 nm ($E_{1cm}^{1\%}$ = 228)
  g. Significant infrared absorption bands measured in KBr disc method in wave numbers (cm$^{-1}$): 3330, 3160 (shoulder), 2900, 2850, 1660, 1600, 1505, 1485, 1400, 1375, 1295, 1230, 1180, 1130, 1065, 910, 780, 700, 480,
  h. Color reactions:
  Greig-Leaback reaction: positive
  Sakaguchi reaction: positive
  Potassium permanganate reaction: positive
  Anilin phthalate reaction: doubtful positive
  Ninhydrine reaction: doubtful positive
  Pauly reaction: negative
  Ehrlich reaction: negative
  Dragendorff reaction: negative
  Barton reaction: negative
  Bentidine periodate: negative
  Ferric chloride-sulfosalicylic acid reaction: negative.
2. A compound as claimed in claim 1, wherein the acid addition salt is hydrochloride which has the following properties:
  a. Melting point: 224° C (decomp.)
  b. Elemental analysis: C, 38.81 ± 1.5%; H, 5.75 ± 0.5%; N, 18.25 ± 1.0%
  c. Specific rotation: $[\alpha]_D^{25}$ = +81.3° ± 10° (c=0.5, H$_2$O); + 63.3° ± 10° (c=0.5, 1/10 N HCl)
  d. Ultraviolet absorption spectrum: $\lambda_{max}^{pH\,7}$ 272 nm ($E_{1cm}^{1\%}$ = 142) $\lambda_{max}^{1/10\,N\,NaOH}$ 272 nm ($E_{1cm}^{1\%}$ = 147) $\lambda_{max}^{1/10\,N\,HCl}$ 280 nm ($E_{1cm}^{1\%}$ = 213).
3. A compound as claimed in claim 1, wherein the acid addition salt is formate which has the following properties:
  a. Melting point: 228° C (decomp.)
  b. Elemental analysis: C, 40.50 ± 1.5%; H, 5.77 ± 0.5%; N, 18.55 ± 1.0%
  c. Specific rotation: $[\alpha]_D^{25}$ = +88.4° ± 10° (c=0.5, H$_2$O); +66.9° ± 10° (c=0.5, 1/10 N HCl)
  d. Ultraviolet absorption spectrum:
  $\lambda_{max}^{pH\,7}$ 271 nm ($E_{1cm}^{1\%}$ = 142)
  $\lambda_{max}^{1/10\,N\,NaOH}$ 271 nm ($E_{1cm}^{1\%}$ = 139)
  $\lambda_{max}^{1/10\,N\,HCl}$ 280 nm ($E_{1cm}^{1\%}$ = 210).
4. A composition for controlling plant diseases, which comprises as the active ingredient a fungicidally effective amount of a member selected from the group consisting of an antibiotic B-98891 and an acid addition salt thereof and a carrier therefor.
5. The composition claimed in claim 4 wherein the composition is in a liquid form and the content of the active ingredient is from about 1% to about 70% by weight relative to the composition.
6. The composition claimed in claim 4 wherein the composition is in a powder form and the content of the active ingredient is from about 0.01% to about 10% by weight relative to the composition.
7. The composition claimed in claim 4 wherein the composition is in an oil form and the content of the active ingredient is from about 0.01% to about 10% by weight relative to the composition.

8. A composition for controlling plant diseases, which contains a fungicidally effective amount of crude antibiotic B-98891 or an acid addition salt thereof over about 50 percent in purity and a carrier therefor.

9. A process for producing Antibiotic B-98891, which comprises culturing *Streptomyces rimofaciens* No. B-98891 (ATCC 31120) in a culture medium containing an assimilable carbon source and a digestible nitrogen source under aerobic conditions until the antibiotic has accumulated in the culture medium, and recovering the antibiotic therefrom.

* * * * *